US010357408B2

(12) United States Patent
Nakao et al.

(10) Patent No.: US 10,357,408 B2
(45) Date of Patent: Jul. 23, 2019

(54) DISPOSABLE DIAPER WITH LENGTHWISE ADHESIVE REGION THAT CROSS WIDTHWISE ADHESIVE REGIONS AND METHOD OF ITS PRODUCTION

(71) Applicant: UNICHARM CORPORATION, Shikokuchuo-shi, Ehime (JP)

(72) Inventors: Hitomi Nakao, Kanonji (JP); Yusuke Kawakami, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 438 days.

(21) Appl. No.: 15/111,180

(22) PCT Filed: May 22, 2014

(86) PCT No.: PCT/JP2014/063589
§ 371 (c)(1),
(2) Date: Jul. 12, 2016

(87) PCT Pub. No.: WO2014/171556
PCT Pub. Date: Oct. 23, 2014

(65) Prior Publication Data
US 2016/0331595 A1  Nov. 17, 2016

(30) Foreign Application Priority Data

Jan. 14, 2014 (JP) ................. 2014-004460

(51) Int. Cl.
*A61F 13/64*  (2006.01)
*A61F 13/494*  (2006.01)
(Continued)

(52) U.S. Cl.
CPC .. *A61F 13/15699* (2013.01); *A61F 13/15772* (2013.01); *A61F 13/49011* (2013.01);
(Continued)

(58) Field of Classification Search
CPC .......... A61F 13/15585; A61F 13/15699; A61F 13/15772; A61F 13/49011;
(Continued)

(56) References Cited

U.S. PATENT DOCUMENTS 5,785,696 A * 7/1998 Inoue ................ A61F 13/53717
604/378
2005/0148965 A1* 7/2005 Richlen ............. A61F 13/15756
604/367
(Continued)

FOREIGN PATENT DOCUMENTS

JP  2002-291803 A  10/2002
JP  2007-14538 A  1/2007
(Continued)

OTHER PUBLICATIONS

International Search Report in PCT Application No. PCT/JP2014/063589, dated Jun. 17, 2014.

*Primary Examiner* — Kathryn E Ditmer
(74) *Attorney, Agent, or Firm* — Hauptman Ham, LLP

(57) ABSTRACT

A disposable diaper includes a crotch section sheet member that is long in one direction, a belly side sheet member, and a back side sheet member. The crotch section sheet member includes first adhesive sections having first adhesive-coated regions coated continuously in the lengthwise direction of the crotch section sheet member, and the belly side sheet member and the back side sheet member include second adhesive sections having second adhesive-coated regions coated continuously in the widthwise direction of the crotch section sheet member, at sections where the crotch section sheet member is to contact with the belly side sheet member and the back side sheet member. The crotch section sheet member is bonded to the belly side sheet member and the back side sheet member with the first adhesive-coated
(Continued)

regions and the second adhesive-coated regions crossing each other.

12 Claims, 7 Drawing Sheets

(51) Int. Cl.
 *A61F 13/49* (2006.01)
 *A61F 13/15* (2006.01)
(52) U.S. Cl.
 CPC .. *A61F 13/49017* (2013.01); *A61F 13/49453* (2013.01); *A61F 13/64* (2013.01)
(58) Field of Classification Search
 CPC .......... A61F 13/49017; A61F 13/49058; A61F 13/4906; A61F 13/49453; A61F 2013/49076
 See application file for complete search history.

(56) References Cited

U.S. PATENT DOCUMENTS

| 2009/0157029 | A1 | | 6/2009 | Hornung et al. | |
|---|---|---|---|---|---|
| 2009/0178755 | A1 | | 7/2009 | Hornung et al. | |
| 2010/0059168 | A1 | * | 3/2010 | Endo | A61F 13/15747 156/164 |
| 2010/0286646 | A1 | * | 11/2010 | Takino | A61F 13/49011 604/385.3 |
| 2011/0112496 | A1 | * | 5/2011 | Fukae | A61F 13/551 604/359 |
| 2011/0112500 | A1 | * | 5/2011 | Wenzel | A61F 13/49011 604/385.3 |
| 2012/0035572 | A1 | * | 2/2012 | Ichikawa | A61F 13/496 604/385.3 |
| 2012/0310193 | A1 | * | 12/2012 | Ostertag | A61F 13/15593 604/365 |
| 2013/0123735 | A1 | | 5/2013 | Ichikawa et al. | |
| 2014/0148776 | A1 | * | 5/2014 | Gassner | A61F 13/49011 604/385.24 |
| 2015/0202094 | A1 | * | 7/2015 | Inoue | A61F 13/496 604/385.16 |

FOREIGN PATENT DOCUMENTS

| JP | 2008-194161 A | | 8/2008 |
|---|---|---|---|
| JP | 2008-212232 A | | 9/2008 |
| JP | 2008212232 A | * | 9/2008 |
| JP | 2011-504124 A | | 2/2011 |
| JP | 2011-506005 A | | 3/2011 |
| WO | 2005/067842 A1 | | 7/2005 |
| WO | 2007/114362 A1 | | 10/2007 |
| WO | 2008/143952 A1 | | 11/2008 |
| WO | 2013/171066 A1 | | 11/2013 |

\* cited by examiner

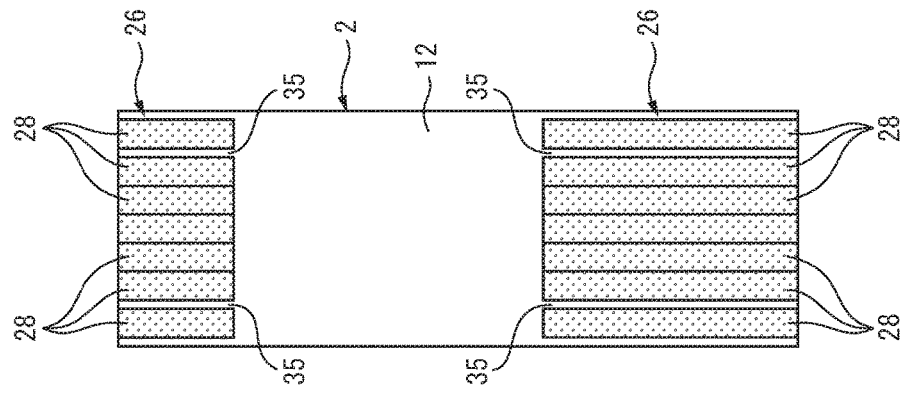
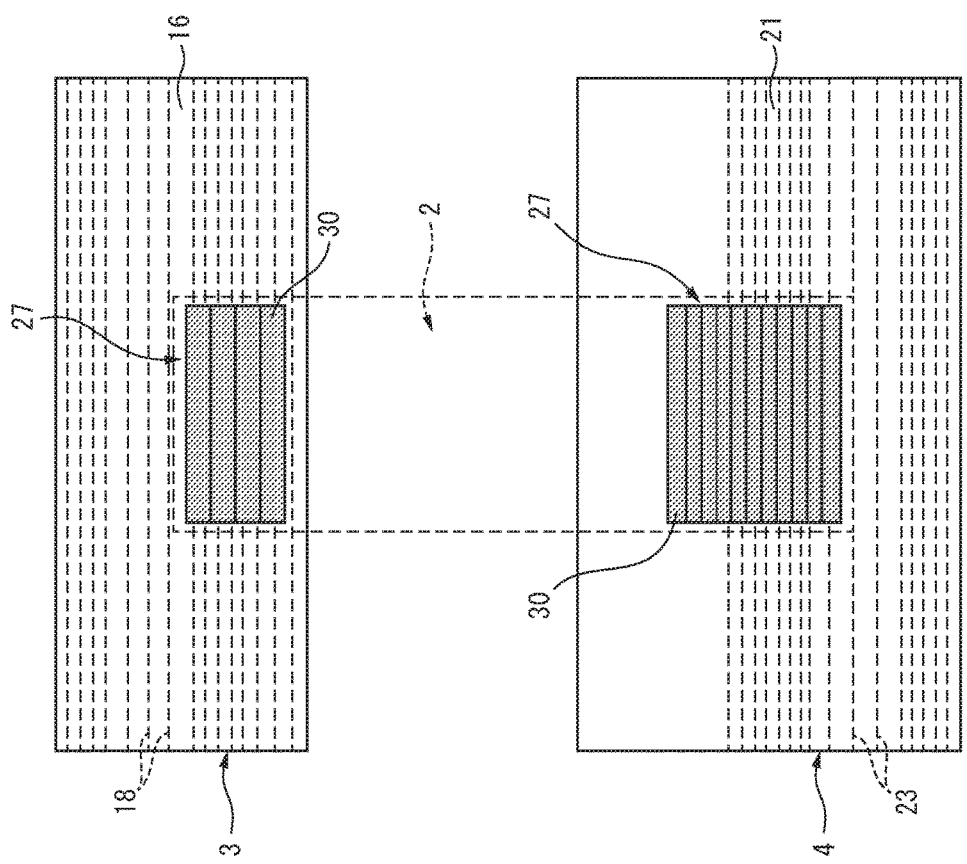

DISPOSABLE DIAPER WITH LENGTHWISE ADHESIVE REGION THAT CROSS WIDTHWISE ADHESIVE REGIONS AND METHOD OF ITS PRODUCTION

RELATED APPLICATIONS

The present application is a National Phase entry of International Application No. PCT/JP2014/063589, filed May 22, 2014, which claims priority of Japanese Application No. 2014-004460, filed Jan. 14, 2014.

TECHNICAL FIELD

The present invention relates to a disposable diaper, and more specifically it relates to a disposable diaper that can exhibit increased strength without impairing comfort when worn.

BACKGROUND ART

There are widely known "3-piece type" disposable diapers that absorb excreted fluids such as urine.

Such 3-piece type disposable diapers are generally provided with a crotch section sheet member that is long in one direction and covers the crotch of the wearer, an belly side sheet member covering the belly side of the wearer, that is connected to one edge side of the lengthwise direction of the crotch section sheet, and a back side sheet member covering the back side of the wearer, that is connected to the other edge side in the lengthwise direction of the crotch section sheet member. The crotch section sheet member, the belly side sheet member and the back side sheet member usually have their joint sections bonded together by an adhesive at the sections where they overlap.

Incidentally, when excreted fluid such as urine has been excreted by the wearer of a disposable diaper, the excreted fluid is absorbed and held by an absorbent body provided in the crotch section sheet member, and therefore the absorbent body draws in excreted fluid each time it is excreted and gradually becomes heavier.

During this time, the weight of the absorbent body increases the overall weight and acts as downward force on the crotch section sheet member to which the absorbent body is attached, such that the crotch section sheet member is pulled downward at the joint sections between the crotch section sheet member and the belly side sheet member or the crotch section sheet member and the back side sheet member.

When this occurs, and there are no measures designed to deal with it, the tensile force accompanying the weight of the absorbent body causes separation and sagging of the crotch section sheet member from the joint sections with the belly side sheet member and/or back side sheet member, potentially damaging the disposable diaper.

Consequently, as described in PTL 1 for example, reinforcing members are provided to reinforce bonding at the sections where the crotch section sheet member overlaps with the belly side sheet member and back side sheet member, so that even when the crotch section sheet member is pulled downward by weight, separation of the crotch section sheet from the belly side sheet member and back side sheet member is prevented.

However, while damage to the disposable diaper is avoided by providing such reinforcing members, the reinforcing member-attached sections become more rigid, causing the sheet members to become hard and stiff, and significantly lowering comfort when worn. Furthermore, since air permeability of the sheet members is inhibited at the sections where the reinforcing members are provided, this can increase unpleasantness for the wearer and has been a cause of reduced comfort.

CITATION LIST

Patent Literature

[PTL 1] Japanese Patent Public Inspection No. 2011-504124

SUMMARY OF THE INVENTION

Technical Problem

The technical problem of the invention is to provide means allowing damage to disposable diapers to be avoided, by causing the crotch section sheet to become separated from the belly side sheet member or back side sheet member when the crotch section sheet member is pulled downward by weight, without impairing comfort for the wearer.

Solution to Problem

In order to solve the problem, according to the present invention, there is provided a disposable diaper comprising a crotch section sheet member that is long in one direction and covers the crotch of the wearer, an belly side sheet member bonded while overlapping with the crotch section sheet member on one edge side of the crotch section sheet in the lengthwise direction, and covering the belly side of the wearer, and a back side sheet member bonded while overlapping with the crotch section sheet member on the other edge side of the crotch section sheet member in the lengthwise direction, and covering the back side of the wearer, the crotch section sheet member being bonded to the belly side sheet member and the back side sheet member with an adhesive at the sections where the crotch section sheet member overlaps the belly side sheet member or the back side sheet member, wherein first adhesive sections provided with first adhesive-coated regions coated continuously in the lengthwise direction of the crotch section sheet members are provided on the side of either the crotch section sheet member or the belly side sheet member and back side sheet member, at the section where the crotch section sheet member is in contact with the belly side sheet member and at the section where the crotch section sheet member is in contact with the back side sheet member, second adhesive sections provided with second adhesive-coated regions coated continuously in the widthwise direction of the crotch section sheet member are provided on the other side, and the crotch section sheet member is bonded to the belly side sheet member and the back side sheet member with the first adhesive-coated regions of the first adhesive sections crossing the second adhesive-coated regions of the second adhesive sections.

In the present invention, the belly side sheet member and the back side sheet member can extend in directions along the widthwise direction of the crotch section sheet member and can be each provided with a plurality of elastic members that elastically expand and contract in the lengthwise direction, wherein at least parts of the elastic members can be disposed at locations corresponding to the first adhesive sections or second adhesive sections provided on the belly side sheet member and back side sheet member, respectively.

Preferably, the belly side sheet member and the back side sheet member are each formed of nonwoven fabrics, and the nonwoven fabrics comprise fibers oriented in the direction along the widthwise direction of the crotch section sheet member.

The first adhesive sections can have a plurality of first adhesive-coated regions arrayed in the widthwise direction of the crotch section sheet member, and among the first adhesive-coated regions, those located on both edges in the widthwise direction of the crotch section sheet member can be arranged with gaps provided between them and the adjacent other first adhesive-coated regions.

It is preferable that the first adhesive sections be provided on both edges in the lengthwise direction of the crotch section sheet member, and that the second adhesive sections be provided on the belly side sheet member and back side sheet member.

In order to solve the aforementioned problem, according to the present invention, there is provided a method for production of a disposable diaper in which one edge side of a crotch section sheet member that is long in one direction and covers the crotch of the wearer is overlaid on an belly side sheet member that covers the belly side of the wearer, and is bonded to the belly side sheet member with an adhesive, and the other edge side of the crotch section sheet member is overlaid on a back side sheet member that covers the back side of the wearer and is bonded to the back side sheet member with an adhesive, wherein first adhesive sections provided with first adhesive-coated regions coated continuously in the lengthwise direction of the crotch section sheet members are formed on the side of either the crotch section sheet member or the belly side and back side sheet members, at the section where the crotch section sheet member is in contact with the belly side sheet member and at the section where the crotch section sheet member is in contact with the back side sheet member, and second adhesive sections provided with second adhesive-coated regions coated continuously in the widthwise direction of the crotch section sheet member are formed on the other side, and then the crotch section sheet member is bonded to the belly side sheet member and the back side sheet member so that the first adhesive-coated regions of the first adhesive sections cross the second adhesive-coated regions of the second adhesive sections.

Preferably, the belly side sheet member and the back side sheet member are each provided with a plurality of elastic members that extend in directions along the widthwise direction of the crotch section sheet member and elastically expand and contract in the lengthwise direction, wherein at least parts of the elastic members are arranged at locations corresponding to the first adhesive sections or second adhesive sections provided on the belly side sheet member and the back side sheet member, respectively.

In the production method according to the present invention, the belly side sheet member and the back side sheet member are each formed of nonwoven fabrics wherein the constituent fibers are oriented in a direction along the widthwise direction of the crotch section sheet member.

Furthermore, in the production method according to the present invention, the first adhesive sections have a plurality of first adhesive-coated regions arrayed in the widthwise direction of the crotch section sheet member, and among the first adhesive-coated regions, those located on both edges in the widthwise direction of the crotch section sheet member are arranged with gaps provided between them and the adjacent other first adhesive-coated regions.

It is preferable that the first adhesive sections be provided on both edges in the lengthwise direction of the crotch section sheet member, and the second adhesive sections be provided on the belly side sheet member and the back side sheet member.

Advantageous Effects of Invention

According to the invention, tensile force is transferred to the first adhesive sections when the crotch section sheet member is pulled downward, while the first adhesive-coated regions that are coated continuously in the lengthwise direction of the crotch section sheet member holding it in a direction so that the crotch section sheet does not fall. Furthermore, at the second adhesive sections where tensile force is transferred from the first adhesive sections, the second adhesive-coated regions that coated continuously in the widthwise direction of the crotch section sheet member and are bonded while crossing with the first adhesive-coated regions, disperse the downward tensile force acting on the first adhesive-coated regions, toward the widthwise direction of the crotch section sheet member.

Consequently, even when the crotch section sheet member is pulled downward by weight, it is possible to hold the crotch section sheet while dispersing the downward force acting on the crotch section sheet member at the first adhesive sections and second adhesive sections. This can stably and reliably maintain bonding between the crotch section sheet member and the belly side sheet member or the crotch section sheet member and the back side sheet member, and prevent separation of the crotch section sheet from the belly side sheet member or back side sheet member and consequent damage to the disposable diaper.

Furthermore, since no members are used that increase the stiffness of the sheet members as in the prior art, where bonding is maintained between the weight-increased crotch section sheet member and the belly side sheet member or the back side sheet member by a reinforcing member, there is no increased stiffness or loss of air permeability of the sheets, and the comfort during wear is also satisfactory.

BRIEF DESCRIPTION OF THE DRAWINGS

FIG. 5 is a diagram schematically showing (a) a state where second adhesive sections have been formed on the belly side sheet member and back side sheet member, and (b) a state where first adhesive sections have been formed on the crotch section sheet member.

DESCRIPTION OF EMBODIMENTS

Figure 1:
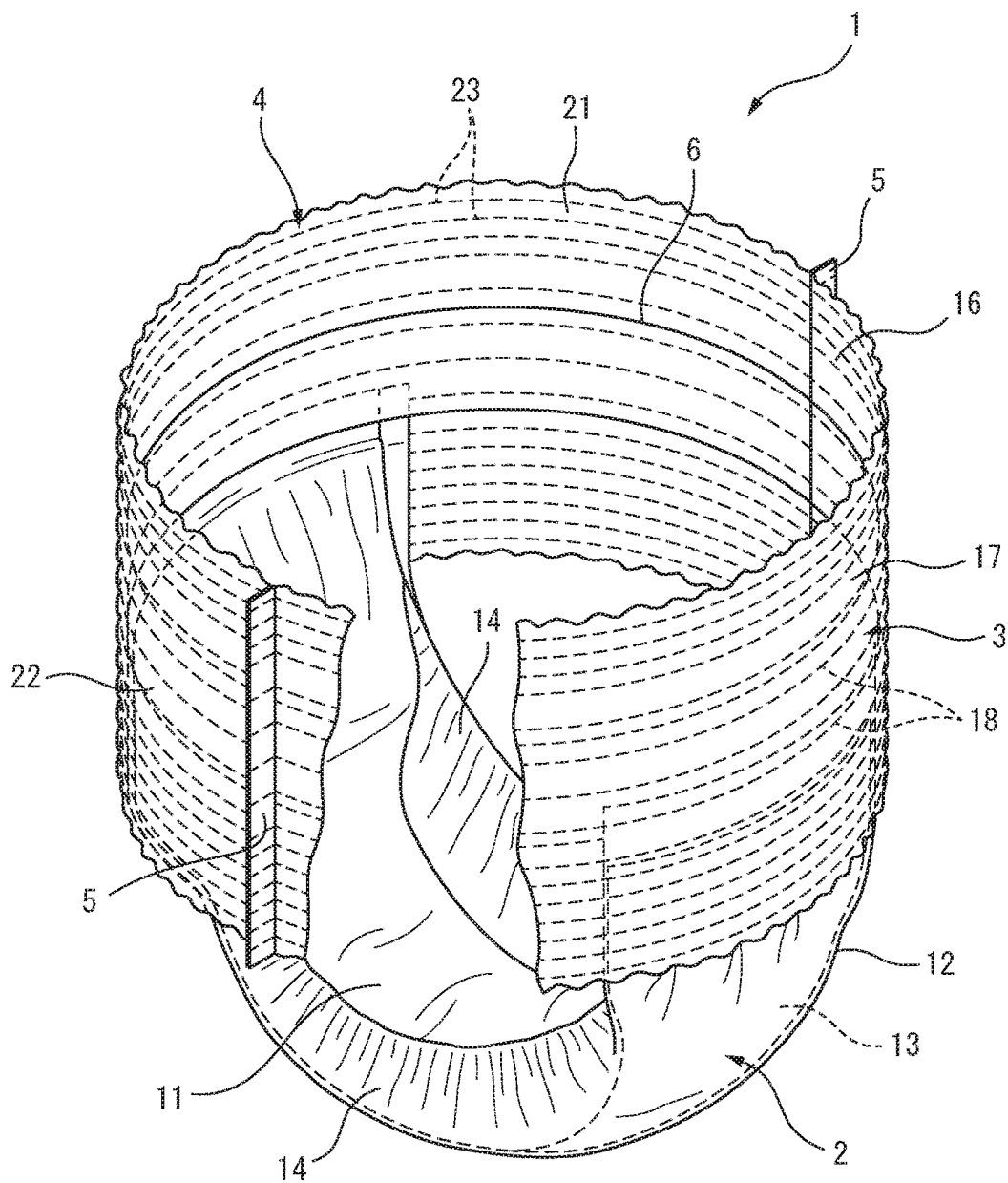
FIG. 1 is a partial cutaway perspective view schematically showing an embodiment of a disposable diaper according to the invention.

FIGS. 1 to 6 show an embodiment of a disposable diaper of the invention, the disposable diaper 1 of this embodiment being a 3-piece type comprising mainly three roughly rectangular sheet members covering the belly side, back side and hip section, respectively, of the wearer.

Specifically, the disposable diaper 1 comprises a crotch section sheet member 2 that is long in one direction and covers across the crotch of the wearer, and an belly side sheet member 3 bonded while overlapping with the crotch section sheet member 2 on one edge side of the crotch section sheet member 2 in the lengthwise direction, and covering the belly side of the wearer. In addition, it comprises a back side sheet member 4 bonded while overlapping with the crotch section sheet member 2 on the other edge side of the crotch section sheet member 2 in the lengthwise direction, and covering the back side of the wearer.

Also, the crotch section sheet member 2 and the belly side sheet member 3 and back side sheet member 4 are bonded together with an adhesive at the sections where they overlap.

The disposable diaper 1 of this embodiment is a pants-type, in which the belly side sheet member 3 and back side sheet member 4 are bonded by any of various means such as fusion.

At both ends of the crotch section sheet member 2 there is attached a band-shaped cover sheet member 6 formed of a nonwoven fabric with excellent flexibility and air permeability, covering the seams where the belly side sheet member 3 and the back side sheet member 4 are bonded to the crotch section sheet member 2 and thereby improves the feel on the skin.

The crotch section sheet member 2 is formed in an essentially rectangular planar shape, extending from the belly side sheet member 3 through the lower end of the hip section of the wearer toward the back side sheet member 4.

The crotch section sheet member 2 is provided with a liquid-permeable sheet 11 (or "top sheet") that has liquid permeability, located on the skin side of the wearer, and a liquid-impermeable sheet 12 (or "back sheet") that has liquid-impermeability, located on the side opposite the skin side of the wearer.

It is also provided with an absorbent body 13 extending in one direction, disposed between the liquid-permeable sheet 11 and the liquid-impermeable sheet 12, that absorbs and retains excreted fluid such as urine that has been excreted by the wearer, and a pair of anti-leakage walls 14 extending along the absorbent body 13 in the lengthwise direction of the crotch section sheet member 2.

The absorbent body 13 has essentially an absorbent body core that absorbs and retains excreted fluid, and a cover sheet with liquid permeability, that covers the outer side of the absorbent body core. Also, for this embodiment, a groin section bent into a raised section toward the center in the widthwise direction of the absorbent body 13, is formed on both edges of the absorbent body core in the widthwise direction, so that the absorbent body 13 easily fits the base of the thighs of the wearer.

The liquid-permeable sheet 11 contacts with the skin of the wearer and rapidly absorbs urine of the wearer, transferring it to the absorbent body 13, and it is formed in an essentially planar rectangular shape that is long in one direction, and specifically the lengthwise direction of the absorbent body 13, and is larger overall than the absorbent body 13, and is mutually bonded with the absorbent body 13 by any desired bonding means such as adhesion with a hot-melt adhesive.

The liquid-permeable sheet 11 is formed of a nonwoven fabric, a woven fabric, a synthetic resin film with liquid-permeation holes formed therein, or a net-like sheet having mesh openings, and it extends in the direction along the lengthwise direction of the absorbent body.

According to the invention, the nonwoven fabric to be used in the liquid-permeable sheet may be made of, for example, natural fibers (wool, cotton or the like), regenerated fibers (rayon, acetate and the like), or synthetic resin fibers (polyolefins such as polyethylene, polypropylene, polybutylene, ethylene-vinyl acetate copolymer, ethylene-ethyl acrylate copolymer, ethylene-acrylic acid copolymer, and ionomer resins; polyesters such as polyethylene terephthalate, polybutylene terephthalate, polybutylene terephthalate and polylactic acid, and polyamides such as nylon).

The nonwoven fabric may be combined with composite fibers such as core-sheath fibers, side-by-side fibers and sea/island fibers, hollow type fibers; irregularly shaped fibers such as flat fibers, Y-shaped fibers or C-shaped fibers; solid crimped fibers such as latent crimped or developed crimped fibers, or split fibers that have been split by a physical load such as a water stream, heat, embossing or the like.

On the other hand, the liquid-impermeable sheet 12 prevents penetration of excreted fluid and prevents leakage of the excreted fluid to the exterior, and it is mutually bonded with the absorbent body 13 by any desired bonding means such as adhesion with a hot-melt adhesive.

The liquid-impermeable sheet 12 is formed in an essentially planar rectangular shape that is long in one direction, and specifically the lengthwise direction of the absorbent body 13, and it is larger overall than the absorbent body 13 and is mutually bonded with the absorbent body 13 by any desired bonding means such as adhesion with a hot-melt adhesive.

Examples for the liquid-impermeable sheet include waterproof-treated nonwoven fabrics, films of synthetic resins (for example, polyethylene, polypropylene, polyethylene terephthalate and the like), and SMS nonwoven fabrics having highly water-resistant meltblown nonwoven fabrics sandwiched by high-strength spunbond nonwoven fabrics.

Also, the absorbent body core of the absorbent body 13 comprises a water-absorbing material such as pulp and a highly absorbent material such as a water-absorbent polymer, and extends from the belly side sheet member side downward to the hip section of the wearer and toward the back side sheet member side, while being formed in the shape of a band with a fixed thickness.

Examples of water-absorbing materials to form the absorbent body core according to the invention include wood pulp obtained using a conifer or broadleaf tree material as the starting material (for example, mechanical pulp such as groundwood pulp, refiner ground pulp, thermomechanical pulp and chemithermomechanical pulp; chemical pulp such as Kraft pulp, sulfide pulp and alkaline pulp; and semichemical pulp); mercerized pulp or crosslinked pulp obtained by chemical treatment of wood pulp; nonwood pulp such as bagasse, kenaf, bamboo, hemp and cotton (for example, cotton linter); regenerated cellulose such as rayon and fibril rayon; and semi-synthetic celluloses such as acetates and triacetates, among which ground pulp is preferred from the viewpoint of low cost and easy shaping.

Examples of highly absorbent materials include starch-based, cellulose-based and synthetic polymer high-water-absorbing materials. Examples of starch-based or cellulose-based high-water-absorbing materials include starch-acrylic acid (acrylate) graft copolymer, saponified starch-acrylonitrile copolymer and crosslinked sodium carboxymethyl cellulose, and examples of synthetic polymer-based high-water-absorbing materials include polyacrylic acid salt-based, polysulfonic acid salt-based, maleic anhydride salt-based, polyacrylamide-based, polyvinyl alcohol-based, polyethylene oxide-based, polyaspartic acid salt-based, polyglutamic acid salt-based, polyalginic acid salt-based, starch-based and cellulose-based high water-absorbent resins (Superabsorbent Polymers: SAP), among which polyacrylic acid salt-based (especially sodium polyacrylate-based) high water-absorbent resins are preferred. Examples of high-water-absorbing material forms include particulate, filamentous and scaly forms, and in the case of particulates, the particle size is preferably 50 to 1000 µm and more preferably 100 to 600 µm.

The cover sheet of the absorbent body 13 is not particularly restricted so long as it has liquid-permeable and absorbent body-holding properties, and from the viewpoint of low cost and absorbent body-holding properties, it is preferably a tissue composed mainly of ground pulp and formed by a wet method.

Also, the pair of anti-leakage walls 14,14 serve to prevent leakage of excreted fluid between the wearer and the crotch section sheet member 2 to the exterior, by rising up toward the wearer when worn so that the end sides contact with the wearer.

The pair of anti-leakage walls 14,14 basically extend in the lengthwise direction of the absorbent body 13 along both edges of the absorbent body 13 in the widthwise direction. The anti-leakage walls 14,14 are preferably hydrophobic or water-repellent so that they can prevent leakage of excreted fluid, and they may be composed of, for example, a material such as a spunbond nonwoven fabric, SMS nonwoven fabric or air-through nonwoven fabric. Also, an elastic member for the anti-leakage wall, made of filamentous rubber or the like (not shown), is disposed on the top edge side of each of the anti-leakage walls 14,14, extending in the lengthwise direction of the anti-leakage walls 14,14, making it easier for the anti-leakage walls 14,14 to stick firmly to the skin surface of the wearer.

The belly side sheet member 3 is formed into an essentially rectangular form extending in the direction along the widthwise direction of the crotch section sheet member 2, i.e. the left-right direction of the wearer during wear, and therefore the length of the lengthwise direction of the belly side sheet member 3 is made to be greater than the length of the widthwise direction of the crotch section sheet member 2.

More specifically, the belly side sheet member 3 comprises an inner side sheet 16 located on the skin side of the wearer, an outer side sheet 17 located on the side opposite the skin side of the wearer, i.e. on the outer side of the disposable diaper 1, and a plurality of elastic members 18 disposed between the inner side sheet 16 and the outer side sheet 17 and extending in the direction along the widthwise direction of the crotch section sheet member 2, i.e. in the lengthwise direction of the belly side sheet member 3.

The inner side sheet 16 and outer side sheet 17 of the belly side sheet member 3 are formed to the same size and shape using nonwoven fabrics having excellent air permeability. For this embodiment, the inner side sheet 16 and the outer side sheet 17 are formed of the same nonwoven fabrics as the liquid-permeable sheet 11 of the crotch section sheet member 2.

On the other hand, the plurality of elastic members 18 elastically expand and contract in the lengthwise direction, i.e. the lengthwise direction of the belly side sheet member 3 (the direction along the widthwise direction of the crotch section sheet member 2), and for this embodiment there is used rubber formed into a filamentous form. The elastic members 18 are arrayed at a prescribed spacing in the widthwise direction of the belly side sheet member 3, i.e. in the longitudinal direction when worn, and are held between the inner side sheet 16 and the outer side sheet 17. Incidentally, an adhesive is coated on the outer peripheral surface of each of the elastic members 18 and the elastic members 18 bond together the inner side sheet 16 and the outer side sheet 17 by the adhesive.

Also, the back side sheet member 4 is formed into an essentially rectangular form extending in the direction along the widthwise direction of the crotch section sheet member 2, i.e. the left-right direction of the wearer during wear, and therefore the length of the lengthwise direction of the back side sheet member 4 is made to be greater than the length of the widthwise direction of the crotch section sheet member 2.

The back side sheet member 4 is also formed to have a greater length in the direction along the lengthwise direction of the crotch section sheet member 2, i.e. in the widthwise direction of the back side sheet member 4 (the vertical direction when worn), than the length in the widthwise direction of the belly side sheet member 3, so as to cover the gluteal region of the wearer when worn.

Specifically, the back side sheet member 4 comprises an inner side sheet 21 located on the skin side of the wearer, an outer side sheet 22 located on the side opposite the skin side of the wearer, i.e. on the outer side of the disposable diaper 1, and a plurality of elastic members 23 disposed between the inner side sheet 21 and the outer side sheet 22 and extending in the direction along the widthwise direction of the crotch section sheet member 2, i.e. in the lengthwise direction of the back side sheet member 4.

The back side sheet member 4 and the belly side sheet member 3 are bonded together at joints 5 on both ends in the lengthwise direction of the back side sheet member 4 and belly side sheet member 3, so as to closely fit around the waist or around the belly of the wearer.

The inner side sheet 21 and outer side sheet 22 of the back side sheet member 4 are formed to the same size and shape using nonwoven fabrics having excellent air permeability. For this embodiment, the inner side sheet 21 and outer side sheet 22 can be formed by the same nonwoven fabrics as the liquid-permeable sheet 11 of the crotch section sheet member 2 or the inner side sheet 16 and outer side sheet 17 of the belly side sheet member 3.

On the other hand, the plurality of elastic members 23 extend in the direction along the widthwise direction of the crotch section sheet member 2 and elastically expand and contract in the lengthwise direction, and for this embodiment there is used rubber formed into a filamentous form. The elastic members 23 are arrayed at a prescribed spacing in the widthwise direction of the back side sheet member 4, i.e. in the longitudinal direction when worn, and are held between the inner side sheet 21 and the outer side sheet 22 of the back side sheet member 4. Incidentally, an adhesive is coated on the outer peripheral surface of each of the elastic members 23 and the elastic members 23 bond together the inner side sheet 21 and the outer side sheet 22 by the adhesive.

For this embodiment, the belly side sheet member 3 and back side sheet member 4 are each formed of a nonwoven fabric as described above, the nonwoven fabrics having the fibers composing the nonwoven fabrics being oriented in the direction along the widthwise direction of the crotch section sheet member 2, i.e. in the lengthwise direction of the belly side sheet member 3 and the back side sheet member 4.

The constituent fibers of the nonwoven fabric forming the belly side sheet member 3 and back side sheet member 4 are oriented in the direction along the widthwise direction of the crotch section sheet member 2 in this manner so as to inhibit the crotch section sheet member 2 from sagging downward by the action of the fibers of the belly side sheet member 3 and the back side sheet member 4 themselves, when the belly side sheet member 3 and the back side sheet member 4 are pulled downward by the weight of the crotch section sheet member 2.

In other words, when the joint sections of the belly side sheet member and back side sheet member with the crotch section sheet member are pulled downward by the weight of the crotch section sheet member, the constituent fibers of the belly side sheet member and the back side sheet member cause the downward force acting on the joint sections to be dispersed in the direction along the widthwise direction of the crotch section sheet member. This minimizes sagging of the crotch section sheet member when the joint sections are pulled up.

In the nonwoven fabrics forming the belly side sheet member 3 and back side sheet member 4, preferably at least 60% of the fibers of the nonwoven fabrics are oriented in the direction along the widthwise direction of the crotch section sheet member 2, i.e. the lengthwise direction of the belly side sheet member 3 and the back side sheet member 4, within a range that can ensure the strength required for the belly side sheet member 3 and back side sheet member 4.

On both edges in the lengthwise direction of the crotch section sheet member 2, and on the belly side sheet member 3 and back side sheet member 4, at the sections where the crotch section sheet member 2 and the belly side sheet member 3 or the back side sheet member 4 are mutually overlapping and in contact, there are provided adhesive sections that bond them together with an adhesive. Consequently, the crotch section sheet member 2 and belly side sheet member 3 and the crotch section sheet member 2 and back side sheet member 4 are each bonded by adhesive sections.

Specifically, first adhesive sections 26 are formed at the sections of the crotch section sheet member 2 where the crotch section sheet member 2 is to be in contact with the belly side sheet member 3 or the back side sheet member 4, i.e. at both edges in the lengthwise direction of the crotch section sheet member 2.

Also, second adhesive sections 27 are formed at the sections of the belly side sheet member 3 and back side sheet member 4 that are to contact with respective edges of the crotch section sheet member 2 in the lengthwise direction.

The first adhesive sections 26 are provided with first adhesive-coated regions 28 formed continuously in the lengthwise direction of the crotch section sheet member 2, on the surface that is to contact with the belly side sheet member 3 and back side sheet member 4.

The first adhesive-coated regions 28 have an adhesive 29 coated within the regions of the first adhesive sections 26, from a location on the nearest edge side in the lengthwise direction of the crotch section sheet member 2 toward a location at the center in the lengthwise direction of the crotch section sheet member 2.

For this embodiment, a plurality of first adhesive-coated regions 28 are provided in each first adhesive section 26, arrayed in the widthwise direction of the crotch section sheet member 2.

Here, the first adhesive sections 26 are provided on the crotch section sheet member 2 in order to allow efficient and stable formation of the first adhesive-coated regions 28, and more specifically coating of the adhesive 29, in consideration of the machine direction of the crotch section sheet member 2 during production of the disposable diaper 1.

Normally, a crotch section sheet member is transported in the lengthwise direction of the crotch section sheet member up to a prescribed location before being bonded with the belly side sheet member or back side sheet member, with the adhesive being coated during transport. During this time, coating of the adhesive during transport of the crotch section sheet member is most efficient if it is coating along the lengthwise direction which is the machine direction of the crotch section sheet member, and since this will also allow the coating itself to be accomplished easily without errors, more stable coating can be carried out.

For this embodiment, therefore, the first adhesive sections 26 provided with the first adhesive-coated regions 28 coated continuously in the lengthwise direction of the crotch section sheet member 2 are provided on the crotch section sheet member 2.

The adhesive to be coated on the first adhesive-coated regions may be any desired one, but it is most preferably a hot-melt adhesive.

Examples of hot-melt adhesives include polyolefins (for example, polyethylene and polypropylene), ethylene/vinyl acetate copolymer-based adhesives, and synthetic rubbers (for example, styrene-based polymers, butadiene-based polymers and isoprene-based polymers such as styrene-isoprene-styrene (SIS), styrene-butadiene-styrene (SBS) or styrene-ethylene-butylene-styrene (SEBS)).

Other adhesives that may be used include acrylic resin-based pressure-sensitive adhesives.

The coating pattern of the adhesive 29 to be coated on the first adhesive-coated regions 28 may be any desired one, and for example, there may be used a coating pattern such as a spiral, omega ($\Omega$), folding line, curved line, straight line (bead) or band-shape that is wider than a straight linear coating pattern.

The coating pattern for the adhesive 29 does not need to be a coating pattern in which the adhesive 29 is coated continuously within the first adhesive-coated regions 28, considering that the first adhesive-coated regions 28 themselves are coated continuously in the lengthwise direction of the crotch section sheet member 2.

In other words, the adhesive 29 may be coated intermittently in a dot or dashed manner in the lengthwise direction of the crotch section sheet member 2, within the first adhesive-coated regions 28.

Also, the method of coating the adhesive 29 may be any desired method, including a method of injecting the adhesive through one or a plurality of nozzles and coating different linear or punctiform coating patterns, a method of contacting it with the section that is to be coated using a roll or the like to coat the adhesive on the surface or as a surface dot pattern, or a method of injecting and coating the adhesive through a nozzle in the shape of a band.

The coating amount of the adhesive 29 for each of the first adhesive-coated regions 28 will depend on the total number of first adhesive-coated regions 28 in each first adhesive section 26, their lengths and the coating pattern of the adhesive 29, but it is preferably 2 to 25 g/m², more preferably 4 to 22 g/m² and even more preferably about 5 to 19 g/m².

If it is less than 2 g/m², the adhesive force will be insufficient and adequate bonding will not be achieved with the second adhesive sections, potentially leading to easy peeling, and conversely if it is greater than 25 g/m² each of the sheet members 2-4 will be hardened by the adhesive 29, potentially creating stiffness.

For the plurality of first adhesive-coated regions 28 in this embodiment, as shown in FIG. 5(b), the first adhesive-coated regions 28, 28 located on both edges in the widthwise direction of the crotch section sheet member 2 among the first adhesive-coated regions 28 are disposed with gaps 35 between them and the adjacent other first adhesive-coated regions 28.

The first adhesive-coated regions 28, 28 located on both edges in the widthwise direction of the crotch section sheet member 2 are disposed in this manner in order to prevent the crotch section sheet member 2 from peeling and falling off from the belly side sheet member 3 or back side sheet member 4 at the first adhesive-coated regions 28, due to force generated by shifting of the crotch section sheet member 2 when the wearer moves.

To explain this point more concretely, when the wearer opens or closes the leg region or is walking, the crotch section sheet member also undergoes bending and twisting in the vertical direction (the lengthwise direction of the crotch section sheet member) and the left-right direction (the widthwise direction of the crotch section sheet member) as the legs of the wearer move.

During this time, force acts in the direction of peeling of the belly side sheet member or back side sheet member by the bending and twisting of the crotch section sheet member at the first adhesive sections, and in particular, force acts from a complex combination of directions at both edges in the widthwise direction of the crotch section sheet member, due to bending and twisting of the crotch section sheet member.

The greatest force considered to be acting on both edges in the widthwise direction of the crotch section sheet member at such times is the force acting toward the center side in the widthwise direction of the crotch section sheet member, and this force causes the crotch section sheet member to be pulled toward the center side in the widthwise direction of the crotch section sheet and weaken bonding between the crotch section sheet member and the belly side sheet member or the back side sheet member, so that an easily peelable state is created.

When the crotch section sheet is in a state of having once been peeled from the belly side sheet member or back side sheet member, and the crotch section sheet member is further bent or twisted, separation between the crotch section sheet member and the belly side sheet member or back side sheet member progresses, thus potentially resulting in the crotch section sheet member falling off from the belly side sheet member or back side sheet member in the worst case.

In particular, since peeling force is easily transmitted to adjacent first adhesive-coated regions when the plurality of first adhesive-coated regions are continuous without gaps in the widthwise direction of the crotch section sheet, weakening of the bonding with the belly side sheet member or back side sheet member at the first adhesive-coated regions located on both edges in the widthwise direction of the crotch section sheet member promotes overall separation from the belly side sheet member or back side sheet member at the first adhesive sections.

For this embodiment, therefore, the first adhesive-coated regions 28, 28 located on both edges in the widthwise direction of the crotch section sheet member 2 are disposed with gaps 35 between them and the adjacent other first adhesive-coated regions 28, and therefore the effect of force acting on the first adhesive-coated regions 28, 28 located on both edges in the widthwise direction of the crotch section sheet member 2 does not spread to the other first adhesive-coated regions.

Thus, even when force acting to peel the crotch section sheet member 2 from the belly side sheet member 3 or back side sheet member 4 acts on the first adhesive-coated regions 28, 28 located on both edges in the widthwise direction of the crotch section sheet member 2, and peeling has actually occurred, that force is not easily transmitted to the adjacent other first adhesive-coated regions 28. As a result, it is easier for the first adhesive sections 26 to maintain bonding of the first adhesive-coated regions 28 other than the first adhesive-coated regions 28, 28 located on both edges in the widthwise direction of the crotch section sheet member 2, making it possible to at least prevent the crotch section sheet member 2 from falling off from the belly side sheet member 3 or back side sheet member 4.

Figure 2:
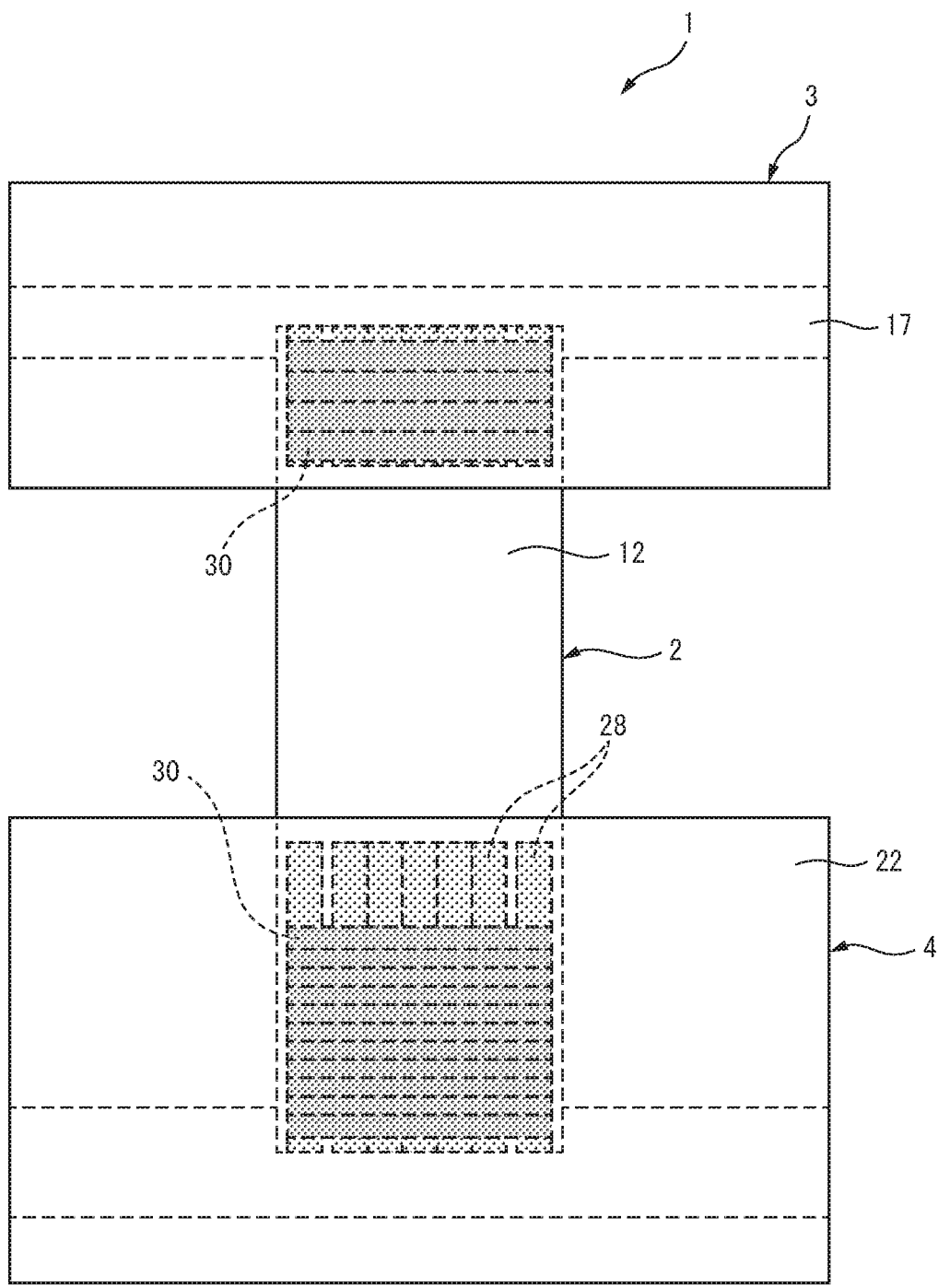
FIG. 2 is a diagram schematically showing an expanded state of the disposable diaper of FIG. 1. The state is shown from the liquid-impermeable sheet side of the crotch section sheet member.
Figure 3:
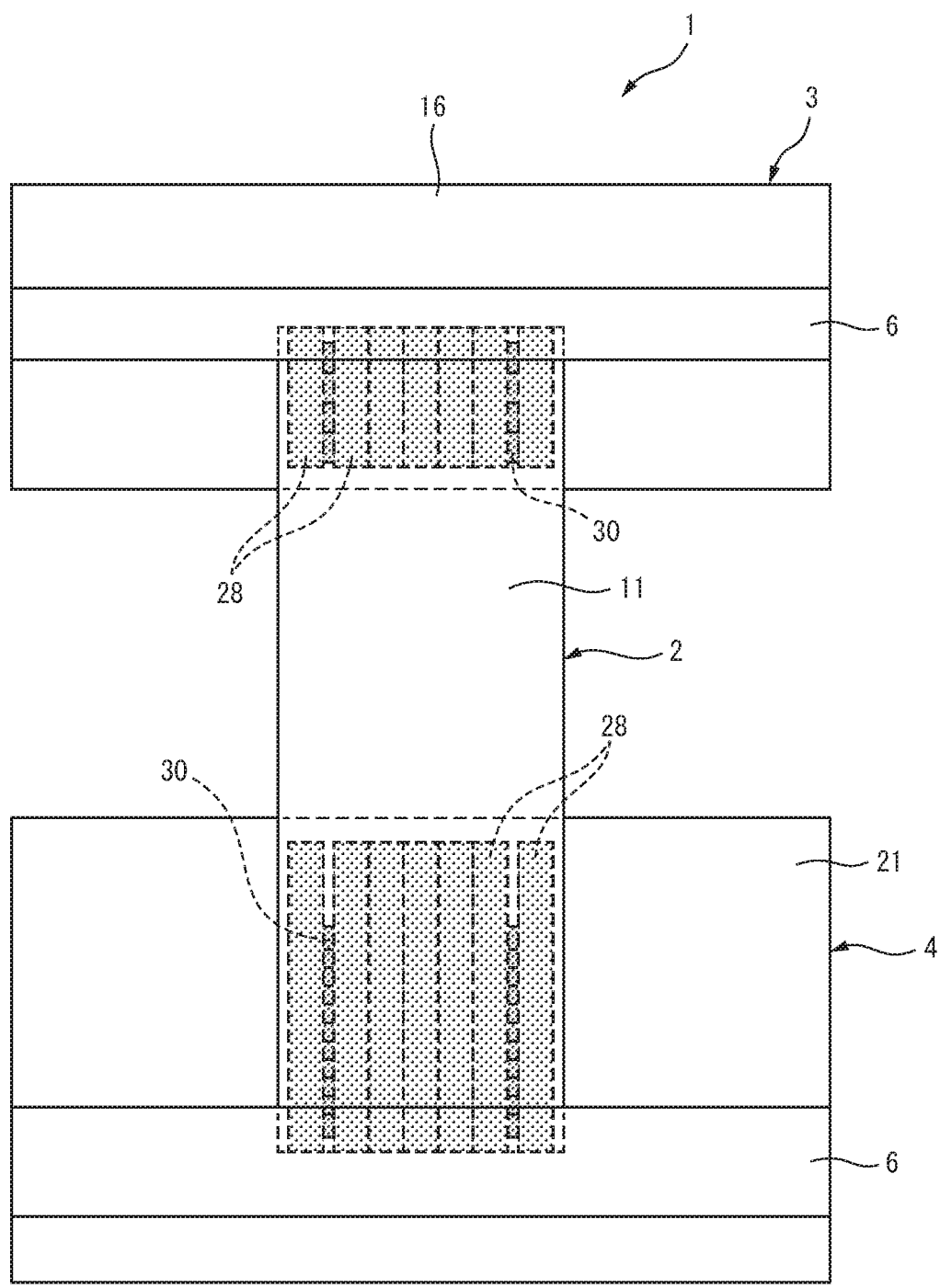
FIG. 3 is a diagram schematically showing an expanded state of the disposable diaper of FIG. 1, from a different direction than FIG. 2. Here, the state is shown from the liquid-permeable sheet side of the crotch section sheet member.
Figure 4:
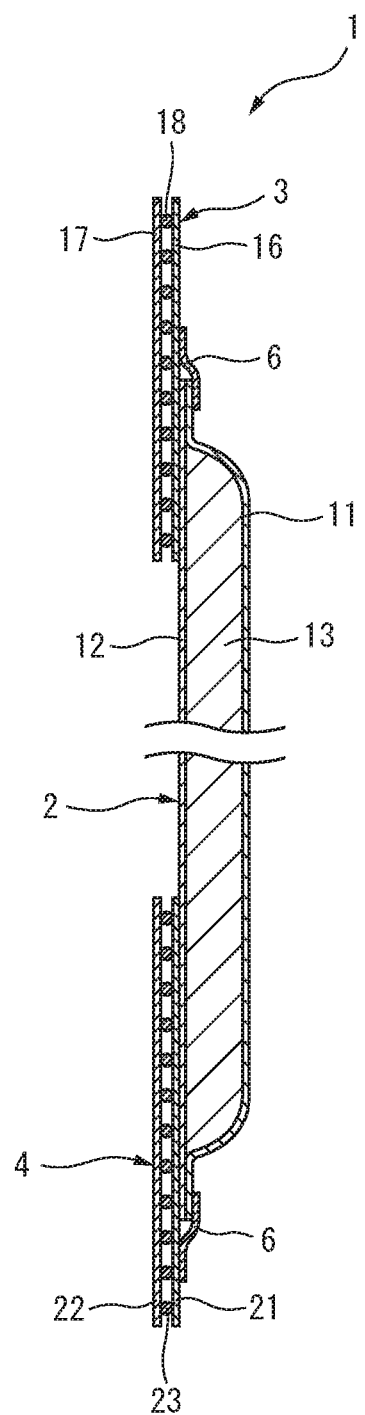
FIG. 4 is a longitudinal section diagram schematically showing an expanded state of the disposable diaper of FIG. 1. Here, the anti-leakage wall is omitted.

In the cases shown in FIG. 2, FIG. 3 and FIG. 5(b), the first adhesive-coated regions 28 other than the first adhesive-coated regions 28, 28 located on both edges in the widthwise direction of the crotch section sheet member 2 are disposed in mutual contact without leaving gaps with the adjacent other first adhesive-coated regions 28. In these cases as well, the adhesive 29 coated onto the first adhesive-coated regions 28 partially contacts or overlaps with the adhesive 29 coated onto the adjacent other first adhesive-coated regions 28, and the adhesive becomes integrated at those sections.

However, the other first adhesive-coated regions 28, i.e. other than the first adhesive-coated regions 28, 28 located on both edges in the widthwise direction of the crotch section sheet member 2, do not necessarily have to contact or overlap with the adjacent first adhesive-coated regions 28, and gaps may be left between them and the adjacent other first adhesive-coated regions 28. In addition, even when the adjacent other first adhesive-coated regions 28 are in contact or overlapping, their adhesives 29 may not be in contact or overlapping depending on the coating pattern, and since it is not absolutely necessary for the adhesive 29 to be in contact or overlapping, an appropriate coating pattern can be freely selected.

On the other hand, the second adhesive sections 27 are provided with second adhesive-coated regions 30 coated continuously in the widthwise direction of the crotch section sheet member 2, i.e. the lengthwise direction of the belly side sheet member 3 and back side sheet member 4, on the contact surface of the crotch section sheet member 2.

The second adhesive-coated regions 30 each have an adhesive 31 coated in the regions of the second adhesive sections 27 on one edge side of each second adhesive section 27, from a location corresponding to one edge side in the widthwise direction of the crotch section sheet member 2 toward a location corresponding to the other edge side.

For this embodiment, in the second adhesive sections 27 there are provided several second adhesive-coated regions 30 arrayed in the lengthwise direction of the crotch section sheet member 2, i.e. the widthwise directions of the belly side sheet member 3 and the back side sheet member 4.

In the case shown in FIG. 2, FIG. 3 and FIG. 5(a), each of the second adhesive-coated regions 30 are disposed in mutual contact without leaving gaps with the adjacent other second adhesive-coated regions 30.

In this case as well, the adhesive 31 coated onto each of the second adhesive-coated regions 30 partially contacts or overlaps with the adhesive 31 coated onto the adjacent other second adhesive-coated regions 30, and the adhesive becomes integrated at those sections.

However, even when the second adhesive-coated regions 30 are in contact or overlapping, their adhesives 31 may not be in contact or overlapping depending on the coating pattern, and since it is not absolutely necessary for the adhesives 31 to be in contact or overlapping, an appropriate coating pattern can be freely selected.

Here, the second adhesive sections 27 are provided on both the belly side sheet member 3 and the back side sheet member 4 in order to allow efficient and stable formation of the second adhesive-coated regions 30, and more specifically coating of the adhesive 31, in consideration of the machine direction of the belly side sheet member 3 and the back side sheet member 4, during production of the disposable diaper 1.

Normally, before being bonded with the crotch section sheet member, the belly side sheet member and back side sheet member are transported to the prescribed location with the lengthwise directions of the belly side sheet member and back side sheet member (i.e., the direction along the widthwise direction of the crotch section sheet member for the disposable diaper) as the machine direction, and the adhesive is coated during this transport. During this time, coating of the adhesive during transport of the belly side sheet member and back side sheet member is most efficient if it is coating along the lengthwise direction which is the machine direction of the belly side sheet member and back side sheet member, and since this will also allow the coating itself to be accomplished easily without errors, more stable coating can be carried out.

For this embodiment, therefore, second adhesive sections 27 each comprising second adhesive-coated regions 30 that coated continuously in the lengthwise directions of the belly side sheet member 3 and back side sheet member 4, or in other words, the direction along the widthwise direction of the crotch section sheet member 2, are provided in both the belly side sheet member 3 and the back side sheet member 4.

The adhesive 31 to be coated on the second adhesive-coated regions 30 is generally preferred to be the same adhesive 29 used for the first adhesive-coated regions 28, and most preferably it is the same hot-melt adhesive as for the first adhesive-coated regions 28. The material of the hot-melt adhesive is the same as for the first adhesive-coated regions 28.

In addition, the coating pattern of the adhesive 31 to be coated on the second adhesive-coated regions 30 is generally preferred to be the same as the coating pattern for the adhesive 29 of the first adhesive-coated regions 28, but it may instead have a different coating pattern. The type of coating pattern and coating method of the adhesive 31 to be coated on the second adhesive-coated regions 30 is basically the same as for the first adhesive-coated regions, and it will therefore not be explained in detail.

The coating amount of the adhesive 31 for each of the second adhesive-coated regions 30 will depend on the total number of second adhesive-coated regions 30 in each second adhesive section 27, their lengths and the coating pattern of the adhesive 31, but it is preferably 2 to 25 $g/m^2$, more preferably 4 to 22 $g/m^2$ and even more preferably about 5 to 19 $g/m^2$. If it is less than 2 $g/m^2$, the adhesive force will be insufficient and adequate bonding will not be achieved with the first adhesive sections 26, potentially leading to easy peeling, and conversely if it is greater than 25 $g/m^2$ each of the sheet members 2-4 will be hardened by the adhesive 31, potentially creating stiffness.

In addition, the crotch section sheet member 2 and belly side sheet member 3 and the crotch section sheet member 2 and the back side sheet member 4 are mutually bonded with the first adhesive-coated regions 28 of the first adhesive sections 26 crossing with the second adhesive-coated regions 30 of the second adhesive sections 27.

Thus, the first adhesive-coated regions 28 contact the second adhesive sections 27 while the second adhesive-coated regions 30 contact with the first adhesive sections 26, with the adhesive 29 to be coated in the first adhesive-coated regions 28 and the adhesive 31 to be coated in the second adhesive-coated regions 30 in a mutually crossed state, and are mutually bonded by the adhesives 29, 31.

The first adhesive-coated regions 28 of the first adhesive sections 26 and the second adhesive-coated regions 30 of the second adhesive sections 27 are crossed in this manner for bonding between the crotch section sheet member 2 and the belly side sheet member 3 and between the crotch section sheet member 2 and the back side sheet member 4 in order to firmly hold the crotch section sheet member 2, that has become heavy by excreted fluid of the wearer, and to avoid its sagging. This also prevents the crotch section sheet member 2 from separating and falling off from the belly side sheet member 3 or back side sheet member 4 due to its own weight.

In other words, as already mentioned, when excreted fluid such as urine has been excreted by the wearer of a disposable diaper, the excreted fluid is absorbed and held by an absorbent body provided in the crotch section sheet member, and therefore the absorbent body of the crotch section sheet member becomes heavier each time it draws in and holds excreted fluid. When this occurs, downward force acts on the crotch section sheet member due to its weight, such that the crotch section sheet member is pulled downward at the joint sections between the crotch section sheet member and the belly side sheet member or the crotch section sheet member and the back side sheet member. Consequently, the tensile force produced by the weight of the crotch section sheet member can lead to separation and falling off of the crotch section sheet member from the joint sections with the belly side sheet member and/or back side sheet member, and in worst cases can potentially cause damage to the disposable diaper.

Figure 6:
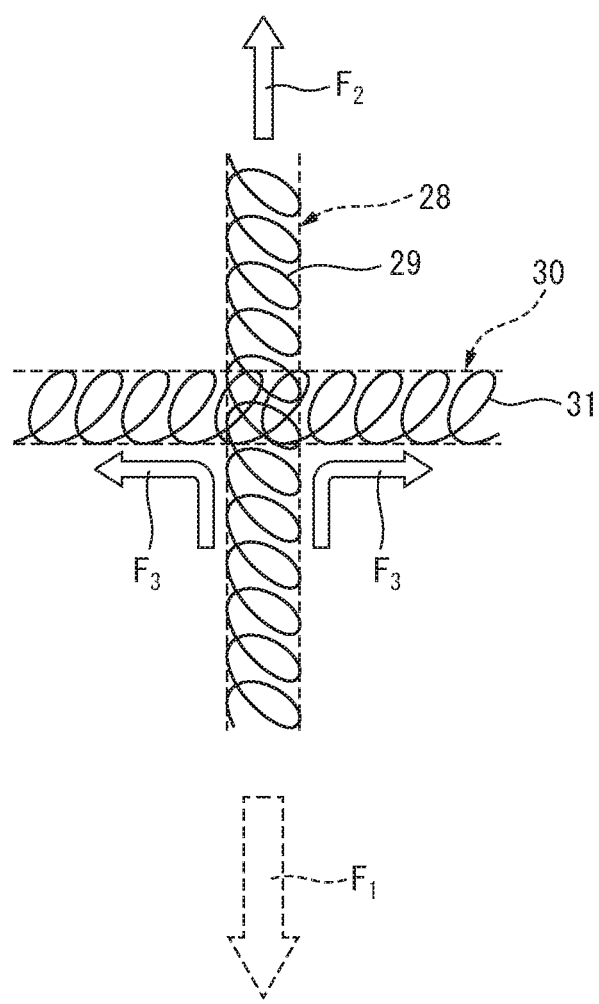
FIG. 6 is a diagram schematically showing the cross-bonded state between a first adhesive-coated region in the first adhesive section and a second adhesive-coated region in the second adhesive section.

According to the invention therefore, as shown in FIG. 6, the first adhesive-coated regions 28 of the first adhesive sections 26 and the second adhesive-coated regions 30 of the second adhesive sections 27 are crossed when bonded, so that when downward force $F_1$ acts on the crotch section sheet member 2 due to the weight of the crotch section sheet member 2, the crotch section sheet member 2 is pulled up by the upward force $F_2$ of the first adhesive-coated regions 28 that coated continuously in the lengthwise direction of the crotch section sheet member 2, thereby being held so as to not sag.

Meanwhile, at the second adhesive-coated regions 30 that are crossing with the first adhesive-coated regions 28, the downward tensile force acting on the first adhesive-coated regions 28 is dispersed in the widthwise direction of the crotch section sheet member 2, and the first adhesive-coated regions 28 are held by a force $F_3$ in the widthwise direction.

In regard to the function of the second adhesive-coated regions, usually an adhesive has high holding power and easily transmits force in the direction in which the coated regions continuously extend, but does not easily transmit force in the direction in which the coated regions do not continuously extend.

Since the second adhesive-coated regions in this case are crossing with the first adhesive-coated regions, when downward tensile force $F_1$ has acted on the first adhesive-coated regions, the force $F_1$ acting on the first adhesive-coated regions is transmitted to the plurality of second adhesive-coated regions that are crossing with the first adhesive-coated regions. Also, the transmitted force $F_1$ is dispersed in the belly side sheet member and/or back side sheet member, in the direction along the widthwise direction of the crotch section sheet member, by the adhesive in the second adhesive-coated regions.

As a result, since it is possible to minimize the load produced by the downward force acting on the first adhesive-coated regions, the crotch section sheet member is resistant to sagging and a raised state can be stably maintained.

As a result, it is possible to stably and reliably maintain bonding between the crotch section sheet member and the belly side sheet member and between the crotch section sheet member and the back side sheet member, and prevent separation of the crotch section sheet from the belly side sheet member or back side sheet member.

In addition, when the first adhesive-coated regions and the second adhesive-coated regions are crossing, the adhesive of the first adhesive-coated regions and the adhesive of the second adhesive-coated regions become mixed at the crossing points, essentially widening the adhesive area. When this occurs, the contact area between the adhesive of the first adhesive-coated regions and the adhesive of the second adhesive-coated regions may be increased at the crossing points and the force more easily dispersed, and this provides the advantage of stably accomplishing dispersion of force from the first adhesive-coated regions to the second adhesive-coated regions.

Incidentally, the belly side sheet member 3 and the back side sheet member 4 are disposed at locations so that at least some of the plurality of elastic members 18, 23 forming the belly side sheet member 3 and back side sheet member 4 correspond to the second adhesive sections 27.

This is so that downward force acting on the joint sections between the second adhesive sections 27 and first adhesive sections 26 due to the weight of the crotch section sheet member 2 is dispersed in the direction along the widthwise direction of the crotch section sheet member 2, i.e. the lengthwise direction of the belly side sheet member 3 and back side sheet member 4, by the elastic members 18, 23.

In other words, when the second adhesive sections 27 of the belly side sheet member 3 and the back side sheet member 4 are pulled downward by the weight of the crotch section sheet member 2, the elastic members 18, 23 at locations corresponding to the second adhesive sections 27 more stably pull up the crotch section sheet member 2 and prevent it from sagging, while also helping to stably maintain the raised state.

A method of producing a disposable diaper having the construction described above will now be explained with reference to FIG. 7.

As the basic flow in the method of producing the disposable diaper, there are carried out, as preliminary steps, a step S1 in which a layered body for the crotch section sheet member is formed and a step S2 in which the composite members for the belly side sheet member and the back side sheet member are formed.

These are followed by a step S3 in which the crotch section sheet member and first adhesive sections are formed from the layered body for the crotch section sheet member, a step S4 in which second adhesive sections are formed in the respective composite members for the belly side sheet member and back side sheet member, and a step S5 in which the crotch section sheet member and the composite members for the belly side sheet member and back side sheet member are bonded.

Also, as finishing steps, there are carried out a step S6 in which the composite member for the belly side sheet member and the composite member for the back side sheet member are overlayed, and a step S7 in which the composite members for the belly side sheet member and back side sheet member are bonded together and cut.

First, as preliminary steps, there are carried out step S1 in which a layered body for the crotch section sheet member is formed and step S2 in which the composite members for the belly side sheet member and the back side sheet member are formed.

In step S1 in which the layered body for the crotch section sheet member is formed, the liquid-permeable sheet that is to compose the crotch section sheet member 2, a liquid-impermeable sheet, an absorbent body and a pair of anti-leakage walls are layered to form a layered body 41 for the crotch section sheet member that is long in the machine direction (the liquid-permeable sheet, liquid-impermeable sheet, absorbent body and pair of anti-leakage walls being formed with long dimensions in the machine direction). Also, the layered body 41 for the crotch section sheet member is transported toward the following step S3 in which the crotch section sheet member and first adhesive section are to be formed.

The layered body 41 for the crotch section sheet member is essentially in a state with a plurality of crotch section sheet members 2 connected in the lengthwise direction, before the individual crotch section sheet members 2 are formed, and in a subsequent step this is cut to predetermined lengths to form the individual crotch section sheet members 2.

On the other hand, in step S2 in which the composite members for the belly side sheet member and back side sheet member are to be formed, the nonwoven fabrics 46 for the long outer side sheets that are to form the outer side sheets 17, 22 of the belly side sheet member 3 and back side sheet member 4 are transported while a plurality of long elastic members 47 that extend in the lengthwise direction of the nonwoven fabrics 46 for the outer side sheets and expand and contract in the lengthwise direction, are placed on the nonwoven fabrics 46 for the outer side sheets, with the lengthwise direction of the elastic members 47 being oriented in the lengthwise direction of the nonwoven fabrics 46 for the outer side sheets.

Also, on the nonwoven fabrics 46 for the outer side sheets on which the long elastic members 47 have been placed, there is further formed a long composite member 49 extending in the machine direction, by layering nonwoven fabrics 48 for the long inner side sheets, which are to form the inner side sheets 16, 21 for the belly side sheet member 3 and back side sheet member 4. The composite members 49 are integrally formed with the composite members 51, 52 for the belly side sheet member and for the back side sheet member, described hereunder.

In addition, while the composite member 49 is being transported in the lengthwise direction, the composite member 49 is cut and separated into two with a cutter 50 at a prescribed location in the widthwise direction of the composite member, to form a composite member 51 for the long belly side sheet member and a composite member 52 for the back side sheet member, in a state before being separated into the individual belly side sheet member 3 and back side sheet member 4.

Each of the composite members 51, 52 for the belly side sheet member and back side sheet member at this stage is in a state with multiple belly side sheet members 3 and back side sheet members 4 connected, and in a subsequent step these will be separated into the individual belly side sheet member 3 and back side sheet member 4. Also, the machine directions of each of the composite members 51, 52 for the belly side sheet member and for the back side sheet member are the respective lengthwise directions of the belly side sheet member 3 and back side sheet member 4.

Next, each of the composite members 51, 52 for the belly side sheet member and for the back side sheet member are kept at a fixed spacing to maintain an arrayed state, while being transported toward the subsequent step S4 in which the second adhesive sections are to be formed.

During formation of the composite member 49, the nonwoven fabric 46 for the outer side sheet and the nonwoven fabric 48 for the inner side sheet are layered with the fibers composing the nonwoven fabrics 46, 48 oriented in the direction along the machine direction. Therefore, each of the composite members 51, 52 for the belly side sheet member and for the back side sheet member are transported in a state with the constituent fibers of the nonwoven fabrics that are to form each of the composite members 51, 52 being oriented in the lengthwise direction of each of the composite members 51, 52.

Therefore, when the individual belly side sheet member 3 and back side sheet member 4 have been separated as parts of the disposable diaper in a subsequent step, the nonwoven fabrics forming both sheet members 3, 4 have the fibers oriented in the lengthwise directions of the belly side sheet member 3 and the back side sheet member 4 (that is, the direction along the widthwise direction of the crotch section sheet member 2).

The reason for which the belly side sheet member 3 and back side sheet member 4 are formed of nonwoven fabrics having the constituent fibers oriented in the direction along the lengthwise direction of the crotch section sheet member 2, and the preferred ranges for the proportion of fibers to be oriented in that direction, were explained above.

Also, in step S3 in which the crotch section sheet member and first adhesive sections are to be formed from the layered body 41 for the crotch section sheet member, the first adhesive sections 26 are formed by coating an adhesive such as a hot-melt adhesive on the liquid-impermeable sheet side of the transported layered body 41 for the crotch section sheet member.

Considering the predetermined length in the lengthwise direction of the crotch section sheet member 2 with respect to the layered body 41 for the crotch section sheet member, the first adhesive sections 26 are at both edges of the sections corresponding to the crotch section sheet member 2, and the adhesive 29 is coated on the sections contacting and overlapping with the belly side sheet member 3 or the back side sheet member 4.

In addition, first adhesive-coated regions 28 are formed continuously toward the lengthwise direction of the crotch section sheet member 2.

For this embodiment, the layered body 41 for the crotch section sheet member is transported with the liquid-impermeable sheet side situated at the top for convenience of production, and therefore the adhesive 29 is coated from above the layered body 41 for the crotch section sheet member.

Also, the layered body 41 for the crotch section sheet member is later to be cut into the individual crotch section sheet members 2, but for this embodiment, when the adhesive 29 is coated, first adhesive sections 26, 26 for each of the crotch section sheet members 2, 2 are formed by simultaneously coating the adhesive 29 on locations of the tail edge at sections corresponding to the preceding crotch section sheet member 2 in the machine direction, and on locations at the leading edge at sections corresponding to the following crotch section sheet member 2, adjacent to the sections corresponding to the preceding crotch section sheet member 2.

Specifically, coating of the adhesive 29 on the layered body 41 for the crotch section sheet member is accomplished considering the predetermined length in the lengthwise direction of the crotch section sheet member 2, and by coating the adhesive 41 at a prescribed spacing, first adhesive-coated regions 28 are provided across both locations on the tail edge of the section corresponding to the preceding crotch section sheet member 2 and the leading edge of the section corresponding to the adjacent following crotch section sheet member 2, and first adhesive sections 26, 26 are simultaneously formed.

For this embodiment, a plurality of first adhesive-coated regions 28 are provided in each first adhesive section 26, arrayed in the widthwise direction of the layered body 41 for the crotch section sheet member.

Here, each of the first adhesive-coated regions 28 is formed toward the lengthwise direction of the layered body 41 for the crotch section sheet member, i.e. the lengthwise direction of the section corresponding to the crotch section sheet member 2, and therefore the adhesive 29 is easily coated during transport on the layered body 41 for the crotch section sheet member being transported in the lengthwise direction, and few coating failures occur. This is therefore advantageous as it is possible to stably accomplish coating of the adhesive 41, and the first adhesive-coated regions 28, and thus the first adhesive sections 26, can be efficiently formed.

Furthermore, for this embodiment, the first adhesive-coated regions 28,28 located on both edges in the widthwise direction of the layered body 41 for the crotch section sheet member, among the plurality of first adhesive-coated regions 28, are disposed with gaps between them and the adjacent other first adhesive-coated regions 28. Thus, the first adhesive-coated regions 28,28 located on both edges in the widthwise direction of the crotch section sheet member 2 are disposed with gaps 35 between them and the adjacent other first adhesive-coated regions 28.

The reason for providing gaps between the first adhesive-coated regions located on both edges in the widthwise direction of the crotch section sheet member 2 and the adjacent other first adhesive-coated regions has already been explained above.

For formation of the first adhesive sections 26, the material and coating pattern of the adhesive 29 of the first adhesive-coated regions 28, and the coating method, may be selected as desired, as explained above.

Figure 7:
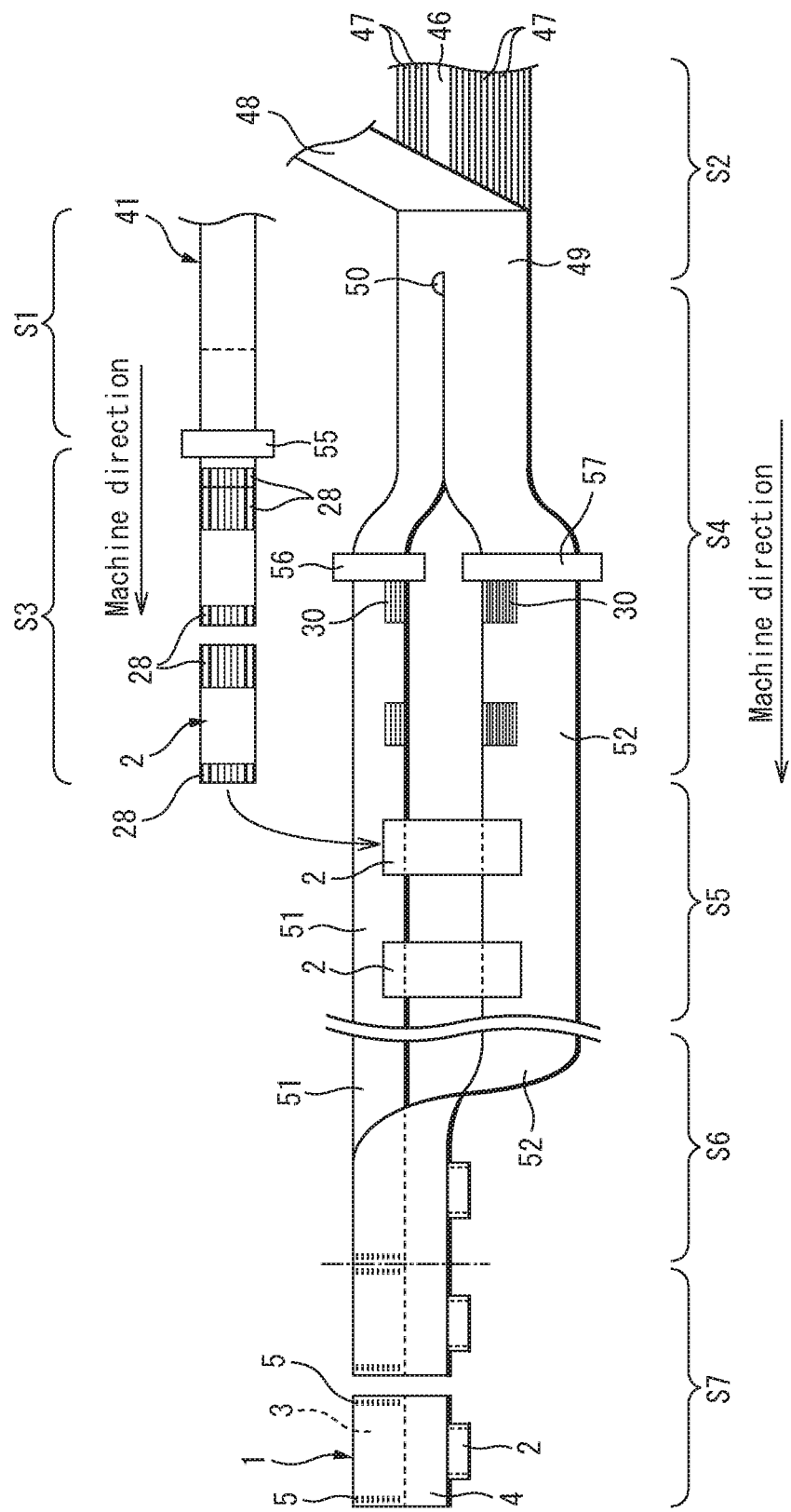
FIG. 7 is a diagram illustrating the production steps for one embodiment of the method of producing of a disposable diaper according to the invention.

The coating method may be accomplished as shown in FIG. 7, for example, using an adhesive coating applicator 55 with a plurality of nozzles (not shown) disposed so as to be directed in the widthwise direction of the crotch section sheet member, simultaneously forming first adhesive-coated regions 28 with a prescribed coating pattern on the top side of the layered body 41 for the crotch section sheet member, i.e. the liquid-impermeable sheet side, during transport.

Also, after the first adhesive sections 26 have been formed, the layered body 41 for the crotch section sheet member is successively cut to predetermined lengths for successive formation of individual crotch section sheet members 2. At this time, the first adhesive sections 26 become formed on both edges of each crotch section sheet member 2.

On the other hand, in step S4 in which second adhesive sections are to be formed on composite members for the belly side sheet member and the back side sheet member, the top sides, i.e. the nonwoven fabrics for the inner side sheets, of the respective composite members 51, 52 for the belly side sheet member and back side sheet member that have been transported, are coated with adhesives such as hot-melt adhesives to form the second adhesive sections 27.

For formation of the second adhesive sections 27, the composite members 51, 52 for the belly side sheet member and back side sheet member are coated with an adhesive 31 at locations corresponding to the sections of contact of the individual belly side sheet member 3 and back side sheet member 4 when they are overlapping with the crotch section sheet member 2, considering the predetermined lengths in the lengthwise direction of the belly side sheet member 3 and back side sheet member 4.

Also, second adhesive-coated regions 30 are provided coated continuously in the lengthwise direction of the respective composite members 51, 52 for the belly side sheet member and back side sheet member.

During formation of the second adhesive sections 27, the adhesive 31 is coated in a prescribed coating pattern by, for example, adhesive coating applicators 56, 57 having a plurality of nozzles (not shown) disposed so as to be directed in the widthwise direction of the composite members 51, 52 for the belly side sheet member and back side sheet member, to simultaneously form a plurality of second adhesive-coated regions 30.

For this embodiment, a plurality of second adhesive-coated regions 30 arrayed in the widthwise direction of the respective composite members 51, 52 for the belly side sheet member and the back side sheet member (i.e. the direction along the lengthwise direction of the crotch section sheet member 2, in the disposable diaper 1), are provided on the second adhesive sections 27.

Since each of the second adhesive-coated regions 30 is formed coating in the lengthwise direction of the respective composite members 51, 52 for the belly side sheet member and for the back side sheet member (i.e. the direction along the widthwise direction of the crotch section sheet member 2 in the disposable diaper 1), it is easy to accomplish coating of the adhesive 31 during transport, on the respective composite members 51, 52 for the belly side sheet member and for the back side sheet member that are being transported in the lengthwise direction, and few coating failures occur. This therefore allows stable coating of the adhesive 31, and the second adhesive-coated regions 30, and thus the second adhesive sections 27, can be efficiently formed.

Furthermore, in step S5 in which the crotch section sheet member is bonded with the composite members for the belly side sheet member and the back side sheet member, both ends of the crotch section sheet member 2 on which the first adhesive sections 26 have been formed are contacted with the respective composite members 51, 52 for the belly side sheet member and for the back side sheet member that each have second adhesive sections 27 formed thereon, to create a firm bond between the first adhesive sections 26 and the second adhesive sections 27.

In addition, the crotch section sheet member 2 and the respective composite members 51, 52 for the belly side sheet member and for the back side sheet member are each bonded in a state with the first adhesive-coated regions 28 of the first adhesive sections 26 crossing with the second adhesive-coated regions 30 of the second adhesive sections 27.

During this time, the composite member 51 for the belly side sheet member and the composite member 52 for the back side sheet member are transported with a fixed distance between them, and the crotch section sheet member 2 is disposed so as to be oriented essentially perpendicular to the lengthwise direction of the respective composite members 51, 52 for the belly side sheet member and for the back side sheet member. This will cause the first adhesive-coated regions 28 and second adhesive-coated regions 29 to be bonded in a crossed state, integrating the adhesive 29 of the first adhesive-coated regions 28 and the adhesive 31 of the second adhesive-coated regions 30 and mutually bonding them.

For this embodiment, since the crotch section sheet member 2 is transported in a state with the liquid-impermeable sheet 12 on which the first adhesive sections 26 have been formed situated on the top side, the crotch section sheet member 2 must contact with the respective composite members 51, 52 for the belly side sheet member and for the back side sheet member after being inverted upside down.

Also, when the crotch section sheet member 2 has contacted the respective composite members 51, 52 for the belly side sheet member and for the back side sheet member, preferably the crotch section sheet member 2 is pressed with a suitable force against the respective composite members 51, 52 for the belly side sheet member and for the back side sheet member, as this will cause the adhesive 29 of the first adhesive-coated regions 28 and the adhesive 31 of the second adhesive-coated regions 30 to become integrated, and be more rigidly bonded together.

Next, in step S6 in which the composite member for the belly side sheet member and the composite member for the back side sheet member are overlayed, the crotch section sheet member 2 is folded to mutually overlay the composite member 51 for the belly side sheet member with the composite member 52 for the back side sheet member that are bonded with the crotch section sheet member.

Also, in step S7 in which the respective composite members for the belly side sheet member and for the back side sheet member are bonded together and cut, the composite member 51 for the belly side sheet member and the composite member 52 for the back side sheet member that have been overlayed are bonded at a fixed width by any desired means such as fusion, leaving fixed spacings so as to match the predetermined lengths of the belly side sheet member 3 and back side sheet member 4 in the lengthwise direction (i.e. the lengths in the direction along the widthwise direction of the crotch section sheet member 2, in the disposable diaper).

The bonded section is then cut to complete the pants-type disposable diaper 1.

As explained above, with a disposable diaper 1 having such a construction, even when the crotch section sheet member 2 is pulled downward by weight, the downward force acting on the crotch section sheet member 2 is pulled up by the first adhesive-coated regions 28 that coated continuously in the lengthwise direction of the crotch section sheet member 2, while the second adhesive-coated regions 30 that coated continuously in the widthwise direction of the crotch section sheet member 2, and are crossing with the first adhesive-coated regions 28, disperse the downward force acting on the first adhesive-coated regions 28.

As a result, it is possible to limit sagging of the crotch section sheet member 2 by the weight of the crotch section sheet member 2, while also stably and reliably maintaining the bonded state between the crotch section sheet member 2 and the belly side sheet member 3 and between the crotch section sheet member 2 and the back side sheet member 4, in order to prevent the crotch section sheet member 2 from separating and falling off from the belly side sheet member 3 or back side sheet member 4, and to prevent damage from occurring in the disposable diaper 1.

Furthermore, since no members are used that increase the stiffness of the sheet members 2-4 as in the prior art, where bonding is maintained between the weight-increased crotch section sheet member and the belly side sheet member and back side sheet member by a reinforcing member, there is no increased stiffness or loss of air permeability of the sheet members 2-4, and the comfort during wear is also satisfactory.

In addition, this production method can stably inhibit sagging of the crotch section sheet member 2 due to the weight of the crotch section sheet member 2, and allows easy production of the disposable diaper 1 that can prevent separation and falling off of the crotch section sheet member 2 from the belly side sheet member 3 or the back side sheet member 4.

According to this embodiment, the first adhesive sections 26 are provided on both edges in the lengthwise direction of the crotch section sheet member 2, while second adhesive sections 27 are provided on the belly side sheet member 3 and back side sheet member 4.

However, the first adhesive sections and second adhesive sections may be formed with the first adhesive sections on one of the sides of the crotch section sheet member and the belly side and back side sheet members, and the second adhesive sections on the other side.

Thus, the first adhesive sections may be formed on the belly side sheet member and back side sheet member and the second adhesive sections on the crotch section sheet member. Alternatively, the first adhesive sections may be formed on one edge side in the lengthwise direction of the crotch section sheet member and the second adhesive sections formed on the other edge side, with the second adhesive sections formed on the belly side sheet member or back side sheet member bonded to the one edge side, and the first adhesive sections formed on the back side sheet member or belly side sheet member bonded to the other edge side.

For this embodiment, the belly side sheet member 3 and back side sheet member 4 are each provided with a plurality of elastic members 18, 23, with at least some of the elastic members 18, 23 disposed at locations corresponding to the second adhesive sections 27 provided on the belly side sheet member 3 and back side sheet member 4.

However, it is not absolutely necessary to dispose the elastic members at locations corresponding to the second adhesive sections, or locations corresponding to the first adhesive sections when the first adhesive sections are disposed on the belly side sheet member and back side sheet member.

Nevertheless, in order to more effectively limit sagging and falling off of the crotch section sheet member, at least some of the elastic members are of course preferably disposed at locations corresponding to the first adhesive sections or second adhesive sections respectively formed on the belly side sheet member and back side sheet member.

According to this embodiment, the nonwoven fabrics forming the belly side sheet member 3 and back side sheet member 4 preferably have the fibers composing the nonwoven fabrics oriented in the direction along the widthwise direction of the crotch section sheet member 2.

However, the constituent fibers of the nonwoven fabrics forming the belly side sheet member and back side sheet member do not necessarily have to be oriented in the direction along the widthwise direction of the crotch section sheet member.

For this embodiment, the first adhesive-coated regions 28, 28 located on both edges in the widthwise direction of the crotch section sheet member 2, among the plurality of first adhesive-coated regions 28 in the first adhesive sections 26, are disposed with gaps provided between them and the adjacent other first adhesive-coated regions 28.

However, the positional relationship of each of the first adhesive-coated regions of the first adhesive sections with the adjacent other first adhesive-coated regions can be basically set as desired, and they may be disposed in contact or overlapping, or they may be disposed with gaps left between them.

Incidentally, for this embodiment a plurality of first adhesive-coated regions 28 are arrayed in the widthwise direction of the crotch section sheet member 2, but a single one may be provided depending on the width of the first adhesive-coated region or the coating pattern of the adhesive.

In addition, this embodiment is a pants-type disposable diaper, in which the belly side sheet member 3 and back side sheet member 4 are bonded by any of various means such as fusion.

However, the disposable diaper of the invention does not necessarily have to be a pants-type, and may instead be an expandable disposable diaper, that connects the belly side sheet member and back side sheet member with fastening tape and target tape when worn. In this mode of the disposable diaper production method, the step of bonding the belly side sheet member and back side sheet member is omitted and replaced with a step of attaching fastening tape and target tape.

REFERENCE SIGNS LIST

1 Disposable diaper
2 Crotch section sheet member
3 Belly side sheet member
4 Back side sheet member
18,23 Elastic members
26 First adhesive section
27 Second adhesive section
28 First adhesive-coated region
29 Adhesive of first adhesive section
30 Second adhesive-coated region
31 Adhesive of second adhesive section

The invention claimed is:

1. A disposable diaper, comprising:
a crotch section sheet member that is elongated in a lengthwise direction and configured to cover a crotch of a wearer,
a belly side sheet member bonded while overlapping with the crotch section sheet member on a side edge of the crotch section sheet in the lengthwise direction, and configured to cover a belly of the wearer, and
a back side sheet member bonded while overlapping with the crotch section sheet member on an opposite side edge of the crotch section sheet member in the lengthwise direction, and configured to cover a back of the wearer, wherein the crotch section sheet member is bonded to the belly side sheet member and the back side sheet member with an adhesive at sections where the crotch section sheet member overlaps the belly side sheet member or the back side sheet member, first adhesive sections including first adhesive-coated regions coated continuously in the lengthwise direction of the crotch section sheet member are provided on either the crotch section sheet member or the belly side sheet member and back side sheet member, at the section where the crotch section sheet member overlaps and is in contact with the belly side sheet member and at the section where the crotch section sheet member overlaps and is in contact with the back side sheet member, second adhesive sections including second adhesive-coated regions coated continuously in a widthwise direction of the crotch section sheet member are provided on the other of the crotch section sheet member or the belly side sheet member and back side sheet member, the first adhesive-coated regions are arrayed in the widthwise direction of the crotch section sheet member, and include a first group of first adhesive-coated regions located on both edges in the widthwise direction of the crotch section sheet member, and a second group of first adhesive-coated regions, the first group of first adhesive-coated regions being adjacent to and spaced away from the second group of first adhesive-coated regions in the widthwise direction, the second group of first adhesive-coated regions includes adjacent first adhesive-coated regions disposed in mutual contact without leaving gaps between one another, and the crotch section sheet member is bonded to the belly side sheet member and the back side sheet member with the first adhesive-coated regions of the first adhesive sections crossing the second adhesive-coated regions of the second adhesive sections.

2. The disposable diaper according to claim 1, wherein the belly side sheet member and the back side sheet member extend along the widthwise direction of the crotch section sheet member and are each provided with a plurality of elastic members configured to elastically expand and contract in the widthwise direction of the crotch section sheet member, and wherein at least parts of the elastic members overlap the first adhesive sections or second adhesive sections provided on the belly side sheet member and back side sheet member, respectively.

3. The disposable diaper according to claim 1, wherein the belly side sheet member and the back side sheet member are each formed of nonwoven fabrics, the nonwoven fabrics comprising fibers oriented along the widthwise direction of the crotch section sheet member.

4. The disposable diaper according to claim 1, wherein the first adhesive sections are provided on both the side edges of the crotch section sheet member in the lengthwise direction, while the second adhesive sections are provided on the belly side sheet member and back side sheet member.

5. The disposable diaper according to claim 1, wherein the first adhesive sections include portions, which are disposed on a side close to a middle portion of the crotch section sheet member in the lengthwise direction and are not bonded to the second adhesive sections.

6. The disposable diaper according to claim 1, wherein the second adhesive-coated regions are disposed in mutual contact without leaving gaps between adjacent second adhesive-coated regions.

7. A method of producing a disposable diaper including a crotch section sheet member that is elongated in a lengthwise direction and configured to cover a crotch of a wearer, a belly side sheet member configured to cover a belly of the wearer and overlaid on and bonded to a side edge of the crotch section sheet in the lengthwise direction, and a back side sheet member configured to cover a back of the wearer and overlaid on and bonded to an opposite side edge of the crotch section sheet in the lengthwise direction, said method comprising:

forming first adhesive sections including first adhesive-coated regions coated continuously in the lengthwise direction of the crotch section sheet members on either the crotch section sheet member or the belly side and back side sheet members, at the section where the crotch section sheet member overlaps and is in contact with the belly side sheet member and at the section where the crotch section sheet member overlaps and is in contact with the back side sheet member, and forming second adhesive sections including second adhesive-coated regions coated continuously in a widthwise direction of the crotch section sheet member on the other of the crotch section sheet member or the belly side sheet member and back side sheet member, and then bonding the crotch section sheet member to the belly side sheet member and the back side sheet member so that the first adhesive-coated regions of the first adhesive sections cross the second adhesive-coated regions of the second adhesive sections, wherein the first adhesive-coated regions are arrayed in the widthwise direction of the crotch section sheet member, and include a first group of first adhesive-coated regions located on both edges in the widthwise direction of the crotch section sheet member, and a second group of first adhesive-coated regions, the first group of first adhesive-coated regions being adjacent to and spaced away from the second group of first adhesive-coated regions in the widthwise direction, and the second group of first adhesive-coated regions includes adjacent first adhesive-coated regions disposed in mutual contact without leaving gaps between one another.

8. The method according to claim 7, wherein the belly side sheet member and the back side sheet member are each provided with a plurality of elastic members that extend along the widthwise direction of the crotch section sheet member and elastically expand and contract in the widthwise direction of the crotch section sheet member, and wherein at least parts of the elastic members overlap the first adhesive sections or second adhesive sections provided on the belly side sheet member and the back side sheet member, respectively.

9. The method according to claim 7, wherein the belly side sheet member and the back side sheet member are each formed of nonwoven fabrics, and wherein the nonwoven fibers are oriented along the widthwise direction of the crotch section sheet member.

10. The method according to claim 7, wherein the first adhesive sections are provided on both the side edges of the crotch section sheet member in the lengthwise direction, and the second adhesive sections are provided on the belly side sheet member and the back side sheet member.

11. The method according to claim 7, wherein the first adhesive sections include portions, which are disposed on a side close to a middle portion of the crotch section sheet member in the lengthwise direction and are not bonded to the second adhesive sections.

12. The method according to claim 7, wherein the second adhesive-coated regions are disposed in mutual contact without leaving gaps between adjacent second adhesive-coated regions.

\* \* \* \* \*